United States Patent
Navia et al.

(10) Patent No.: US 6,709,415 B2
(45) Date of Patent: Mar. 23, 2004

(54) INTRALUMINAL CATHETER WITH EXPANDABLE TUBULAR OPEN-WALLED ELEMENT

(75) Inventors: José Antonio Navia, Buenos Aires (AR); Jorge Luis Jordana, Buenos Aires (AR)

(73) Assignee: BioSud S.A., Buenos Aires (AR)

( * ) Notice: Subject to any disclaimer, the term of this patent is extended or adjusted under 35 U.S.C. 154(b) by 79 days.

(21) Appl. No.: 10/001,061

(22) Filed: Oct. 31, 2001

(65) Prior Publication Data

US 2002/0091354 A1 Jul. 11, 2002

Related U.S. Application Data

(62) Division of application No. 08/935,783, filed on Sep. 23, 1997, now Pat. No. 6,340,356.

(51) Int. Cl.⁷ .............................................. A61M 29/00
(52) U.S. Cl. ........................................................ 604/104
(58) Field of Search ........................ 604/96.01, 101.01, 604/101.05, 104–109, 915, 919; 606/191, 194, 195

(56) References Cited

U.S. PATENT DOCUMENTS

| | | | |
|---|---|---|---|
| 3,467,090 A | 9/1969 | Zollett ......................... 604/104 |
| 4,290,428 A | 9/1981 | Durand et al. ........... 128/349 B |
| 4,459,977 A | 7/1984 | Pizon et al. ................. 128/1 D |
| 4,535,757 A | 8/1985 | Webster, Jr. ................ 128/1 D |
| 4,648,384 A | 3/1987 | Schmukler ................. 128/1 D |
| 4,689,041 A | 8/1987 | Corday et al. ................ 604/53 |
| 4,723,549 A | 2/1988 | Wholey et al. .............. 128/344 |
| 4,850,969 A | 7/1989 | Jackson ........................ 604/96 |
| 4,885,003 A | 12/1989 | Hillstead .................... 604/22 |
| 4,917,667 A | 4/1990 | Jackson ........................ 604/96 |
| 4,921,484 A | 5/1990 | Hillstead .................... 604/104 |
| 4,927,412 A | 5/1990 | Menasche .................... 604/96 |
| 5,002,560 A | 3/1991 | Machold et al. ............ 606/198 |
| 5,033,998 A | 7/1991 | Corday et al. ................ 600/18 |
| 5,034,001 A | 7/1991 | Garrison et al. ............... 604/53 |
| 5,221,261 A | 6/1993 | Termin et al. .............. 604/104 |
| 5,263,963 A | 11/1993 | Garrison et al. ............ 606/198 |
| 5,324,260 A | 6/1994 | O'Neill et al. ................ 604/96 |
| 5,345,927 A | 9/1994 | Bonutti ....................... 606/198 |
| 5,395,331 A | 3/1995 | O'Neill et al. ................ 604/96 |

(List continued on next page.)

FOREIGN PATENT DOCUMENTS

| | | |
|---|---|---|
| EP | 0 385 920 | 9/1990 |
| EP | 0 533 511 | 3/1993 |
| EP | 0 743 047 | 11/1996 |
| WO | WO 94/00178 | 1/1994 |

Primary Examiner—Sharon Kennedy
(74) Attorney, Agent, or Firm—Edward J. Lynch; Duane Morris LLP

(57) ABSTRACT

An intraluminal catheter having an expandable tubular open-walled element for immobilizing at least part of the catheter within a patient's body lumen, generally comprising an elongated shaft and a tubular open-walled element secured to the shaft, wherein the tubular open-walled element is at least in part expandable from an unexpanded diameter to a larger diameter expanded diameter within the body lumen. The expanded diameter configuration is configured to contact a wall defining the body lumen and thereby releasably secure at least part of the catheter within the body lumen. A cannula member, used for delivering or removing fluids from the body lumen, can be positioned in one or more optimal perfusion locations within the body lumen during use, independent of the secured site. When occlusion of the axial flow is necessary, an optional occluding member may be reversibly deployed so that it expands inside and against the expanded tubular open-walled element. The optimal occlusion site can also be chosen independently of the secured site.

5 Claims, 8 Drawing Sheets

U.S. PATENT DOCUMENTS

| | | | |
|---|---|---|---|
| 5,423,745 A | 6/1995 | Todd et al. | 604/53 |
| 5,425,708 A | 6/1995 | Nasu | 604/96 |
| 5,433,700 A | 7/1995 | Peters | 604/4 |
| 5,458,574 A | 10/1995 | Machold et al. | 604/101 |
| 5,464,449 A | 11/1995 | Ryan et al. | 623/1 |
| 5,484,444 A | 1/1996 | Braunschweiler et al. | 606/108 |
| 5,505,698 A | 4/1996 | Booth et al. | 604/96 |
| 5,523,745 A | 6/1996 | Fortune et al. | 340/825.19 |
| 5,553,957 A | 9/1996 | Dornbusch et al. | 401/209 |
| 5,558,644 A | 9/1996 | Boyd et al. | 604/96 |
| RE35,352 E | 10/1996 | Peters | 604/4 |
| 5,584,803 A | 12/1996 | Stevens et al. | 604/4 |
| 5,591,129 A | 1/1997 | Shoup et al. | 604/96 |
| 5,620,417 A | 4/1997 | Jang et al. | 604/96 |
| 5,653,684 A | 8/1997 | Laptewicz et al. | 604/22 |
| 5,662,671 A | 9/1997 | Barbut et al. | 606/170 |
| 5,695,469 A | 12/1997 | Segal | 604/104 |
| 5,695,499 A | 12/1997 | Helgerson et al. | 606/108 |
| 5,755,708 A | 5/1998 | Segal | 604/109 |
| 5,868,708 A | 2/1999 | Hart et al. | 604/104 |
| 5,928,260 A | 7/1999 | Chin et al. | 604/104 |
| 5,976,172 A | 11/1999 | Homsma et al. | 606/200 |

INTRALUMINAL CATHETER WITH EXPANDABLE TUBULAR OPEN-WALLED ELEMENT

This application is a division of patent application Ser. No. 08/935,783 filed Sep. 23, 1997 now U.S. Pat. No. 6,340,356.

BACKGROUND OF THE INVENTION

This invention relates to the field of intraluminal catheters, and more particularly to an intraluminal catheter for cannulation of a patient's body lumen for delivering or draining fluids.

The use of intraluminal catheters in a patient's body lumen often requires securing the catheter so that its distal or operative end is at a desired location inside the body lumen. Means for securing the catheter within a body lumen include purse string sutures, and balloons. When using purse strings, the vessel is usually clamped to stop the flow of fluid inside it. The clamping procedure makes purse strings complicated to use in percutaneous or minimally invasive surgical techniques. Moreover, the clamped site, which must be in close proximity to the cannulation site, may cause trauma to the vessel wall or dislodging of calcium debris or plaque within the vessel.

Use of a balloon on the catheter to secure the catheter within the patient's body lumen may also cause trauma to the lumen, due to the inflation pressure inside the balloon necessary to hold the catheter in place. Moreover, the retention balloon must have a large surface area in contact with the body lumen, for there to be sufficient frictional resistance to prevent catheter displacement. As a result, the large retention balloon is likely to block the opening to nearby branch lumens which intersect the cannulated lumen. Additionally, by using a balloon to both secure the catheter within the body lumen and occlude the lumen, the occluder cannot be displaced relative to the secured site to find the optimum occlusion site. Moreover, because the inflated balloon does not allow for flow of fluid around or across the balloon, the cannulated lumen is obstructed by the balloon, and the catheter cannot be used in procedures where occlusion of the vessel is not desirable.

In some procedures involving cannulae, it may be desirable to occlude the cannulated vessel. For example, during heart surgery, the myocardium is protected by a technique known as retroperfusion in which cardioplegic solution is infused in a retrograde manner (through veins opposite the normal blood flow direction) into the coronary anatomy via the coronary sinus. Retroperfusion requires occlusion of the coronary anatomy to prevent back flow of the cardioplegic solution into the right atrium. On current retroplegia cannulae designs, a balloon is used to retain the cannula in place inside the patient, and also serves to occlude the cannulated vessel. The retention balloon of the current cannulae inflates inside the ostium downstream of the middle cardiac vein (serving the right ventricular territory), in the space between the middle cardiac vein and the veins coming from the left ventricle, and the solution is infused distally to the balloon. Because the space upstream of the middle cardiac vein between the ostium and the middle cardiac vein is too small to contain the balloon, the middle cardiac vein must be excluded from the perfusion. Consequently, the right ventricle is left unprotected during heart surgery. Therefore, although vessel occlusion may be required in a procedure, use of the inflated retention balloon to occlude the vessel is disadvantageous.

Attempts to improve the catheter design to minimize the obstruction the branch lumens have included shortening the retention balloon. Although the use of protuberances or ridges on the balloon surface to improve the frictional contact has been suggested, the shortened balloon may provide insufficient frictional contact with the lumen surface. Fixation balloons made of an open open-walled element material are also known, wherein fluid is free to flow through the open-walled element.

What has been needed and heretofore unavailable is an intraluminal catheter with a securing member which allows for the free flow of fluid around and across it, and with a cannula and an occluder that can be positioned independently the secured site. The present invention satisfies these and other needs.

SUMMARY OF THE INVENTION

The invention is directed to an intraluminal catheter having an expandable tubular open-walled element for securing at least part of the catheter within a patient's body lumen. The intraluminal catheter of the invention generally comprises an elongated shaft and a tubular open-walled element secured to the shaft, wherein the tubular open-walled element is at least in part expandable from an unexpanded diameter configuration to a larger diameter expanded diameter configuration within the body lumen. Upon expansion, the tubular open-walled element is configured to contact a wall defining the body lumen and thereby secure at least part of the catheter within the body lumen. A cannula member, used for delivering or removing fluids from the body lumen, is slidably disposed within a lumen of the shaft and a lumen of the tubular open-walled element.

In one embodiment of the invention, the catheter shaft comprises an outer tubular member and an inner tubular member slidably disposed in a lumen of the outer tubular member. The cannula member is releasably secured to the inner tubular member, and is disposed in a lumen therein. The tubular open-walled element is secured to the inner tubular member, so that when the cannula member is secured to the inner tubular member, the cannula member can be secured within the body lumen by the expanded open-walled element. However, when the cannula member is released from the inner tubular member, it is longitudinally displaceable relative to the inner tubular member. Therefore, the cannula member can be positioned in one or more optimal perfusion locations within the body lumen during use, independent of the secured site, and then releasably locked into position on the secured inner tubular member.

In one embodiment of the invention, an occluding member is slidably disposed a lumen of the shaft. In a preferred embodiment, the occluding member is on the cannula member. However, it can be secured to the inner lumen of the tubular open-walled element instead. When occlusion of the axial flow is necessary, the occluding member may be reversibly deployed so that it expands inside and against the expanded tubular open-walled element. Because the cannula can be moved freely in the axial direction, the occluding member secured thereto can be positioned in the desired site by pushing or pulling the cannula. The optimal occlusion site can be chosen independently of the secured site, and the occluder and cannula secured within the body lumen by being releasably secured to the secured inner tubular member. The secured cannula member can then be used to deliver or remove fluid from an area of the body lumen sectioned off by the occluding member.

However, where such displacement of the occluding member relative to the tubular open-walled element is not required, the inner tubular member is omitted. Thus, in one embodiment, the catheter comprises an elongated shaft, and a cannula member having the tubular open-walled element and the occluding member secured thereto, with the cannula member slidably disposed in the lumen of the elongated shaft.

The open-walled element material allows fluid to flow freely around and across the open-walled element, and generally comprises a mesh structure or a permeable material. Because the open-walled element does not restrict fluid flow, it can be deployed over lateral branches intersecting the patient's body lumen without obstructing the lateral branches or the coaxial flow around the cannula. Unlike fixation balloons which do obstruct flow within the body lumen, the length of the open-walled element does not have to be minimized to avoid obstructing the flow in the body lumen and side branches. Therefore, the open-walled element can be as long as necessary to obtain good support, and minimizes pressure on the vessel wall. The open-walled element may be made of a variety of expandable materials including but not limited to polymeric materials, stainless steel, a NiTi alloy, a pseudoelastic NiTi alloy having a phase transition temperature above body temperature, a cobalt, nickel, molybdenum, and chromium alloy such as MP35N.

In a presently preferred embodiment of the invention, the open-walled element is self expanding, so that the open-walled element assumes an unexpanded configuration in response to radially compressing force, and the expanded diameter configuration when the radially compressing force is removed. However, the open-walled element may be configured to expand in response to a radially expanding force.

One aspect of the invention involves a method of performing a medical procedure using the catheter of the invention. The method comprises positioning the catheter in a desired location within the patient's body lumen, expanding at least a portion of the catheter tubular open-walled element to contact a wall defining the body lumen and secure the catheter therein, and performing the medical procedure. The catheter is released from the body lumen following the medical procedure by collapsing the open-walled element into the unexpanded diameter configuration.

A presently preferred embodiment of the method of the invention involves performing a perfusion procedure within the patient's body lumen, including but not limited to retroperfusion of the heart, perfusion of the ascending aorta, and isolation of a dissection of the descending aorta. For example, in retroperfusion of the heart, using the present invention, the tubular open-walled element can be left outside the coronary sinus ostium, inside the right atrium, and the occluding member can be advanced into the sinus until achieving its closure. Therefore, unlike available retroplegia cannulae, the catheter of the invention allows retroperfusion of the middle cardiac vein, which provides full retroperfusion of the heart, including the right ventricle, otherwise left unprotected with current cannula designs.

The catheter of the invention, having an expandable open-walled element, allows for securing the catheter within a patient's body lumen without occluding side branches intersecting the body lumen. In one embodiment of the invention, the catheter provides for cannulation of the body lumen, wherein the cannula can be displaced relative to the secured site to choose the optimal perfusion site. In another embodiment of the invention, the catheter provides for occlusion of the body lumen, and displacement of the occluding member relative to the secured site so that the optimal occlusion site can be selected. These and other advantages of the invention will become apparent from the following detailed description of the invention and accompanying exemplary figures.

DETAILED DESCRIPTION OF THE INVENTION

Figure 1:
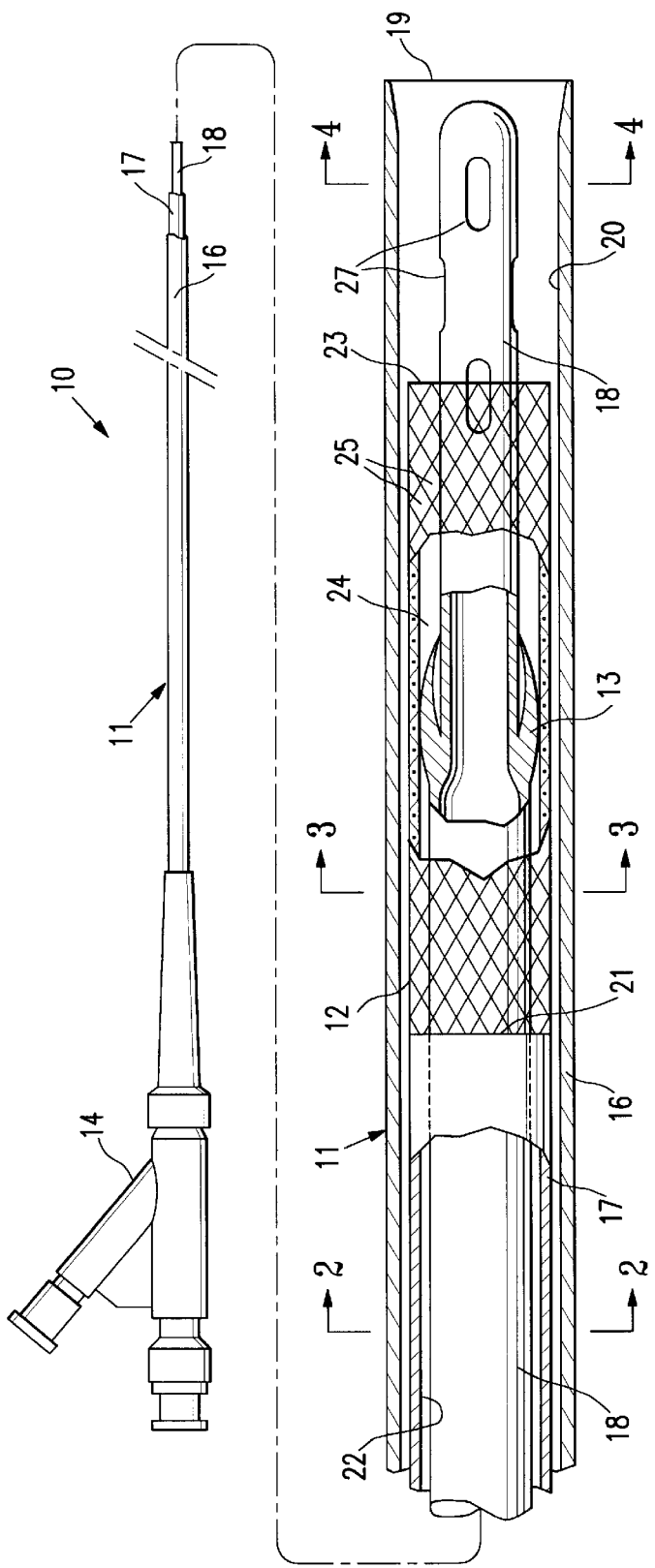
FIG. 1 is an elevational view partially in section of an intraluminal catheter which embodies features of the invention.
Figure 2:
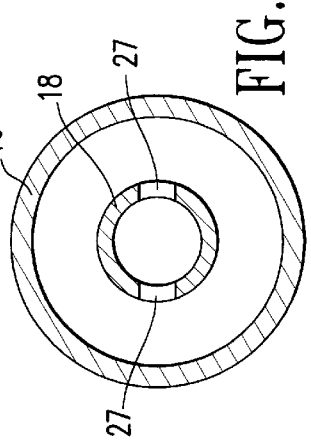
FIGS. 2–4 are transverse cross-sectional views of the catheter shown in FIG. 1 taken along lines 2—2, 3—3, and 4—4, respectively.
Figure 3:
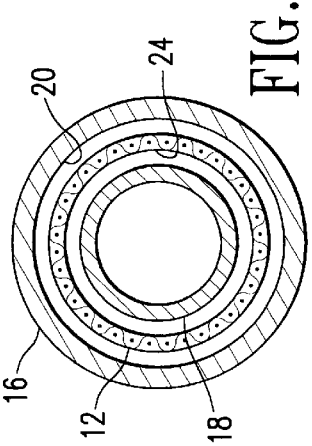
Figure 4:
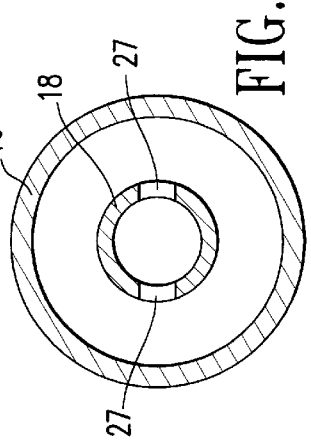

In the embodiment illustrated in FIG. 1, the intraluminal catheter 10 of the invention comprises an elongated shaft 11, a tubular open-walled element 12 secured to the shaft 11, an occluding member 13 on the shaft for reversibly occluding a body lumen, and an adapter 14 mounted on a proximal end of the shaft 11. The shaft comprises an outer tubular member 16, and inner tubular member 17. The outer tubular member 16 has a proximal end and a distal end, a port 19 on the distal end, and a lumen 20 extending therein. The inner tubular member 17 also has a proximal end and a distal end, a port 21 on the distal end, and a lumen 22 extending therein. The inner tubular member 17 is slidably disposed within the lumen 20 of the outer tubular member 16, and cannula member 18 is slidably disposed within the lumen 22 of the inner tubular member 17 and a lumen of the tubular open-walled element 12. FIGS. 2–4 illustrate transverse cross-sections of the catheter 10 shown in FIG. 1 taken along lines 2—2, 3—3, and 4—4 respectively.

Figure 5:
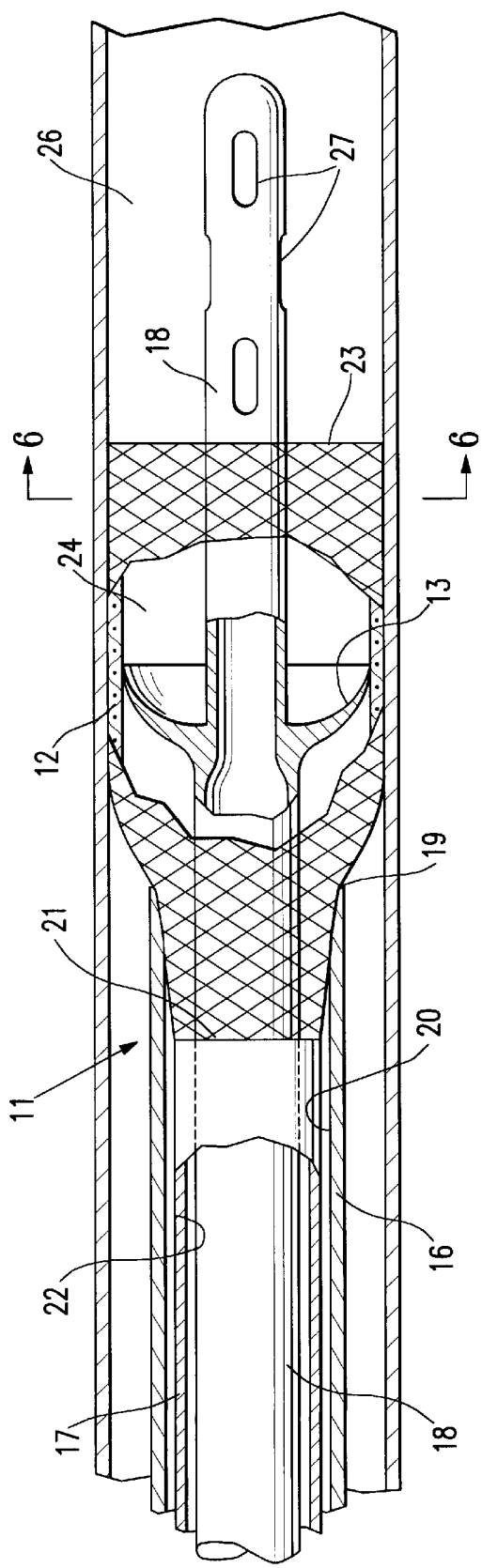
FIG. 5 is an elevational view partially in section of the intraluminal catheter shown in FIG. 1, within a body lumen.
Figure 6:
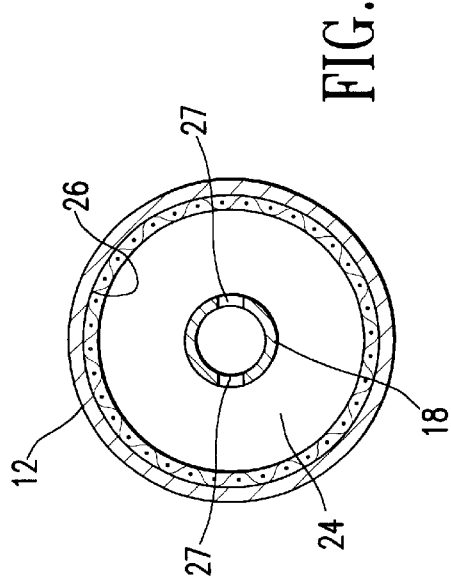
FIGS. 6 is a transverse cross-sectional view of the catheter shown in FIG. 5 taken along lines 6—6.

The tubular open-walled element 12 has proximal and distal ends, a port 23 on the distal end, and a lumen 24. The open-walled element 12 is provided with openings 25 allowing for flow of fluids across a wall of the element 12. The open-walled element 12 proximal end is secured to the distal end of the inner tubular member 17 and the open-walled element 12 distal end is left unsecured. The tubular open-walled element 12 is at least in part expandable to an expanded diameter configuration within a body lumen to contact a wall defining the body lumen and thereby releasably secure the catheter within the body lumen. In FIG. 1, the tubular open-walled element 12 is illustrated in an unexpanded diameter configuration. FIG. 5, which shows the catheter 10 within a body lumen 26, illustrates an expanded diameter configuration of the tubular open-walled element 12 in contact with the body lumen wall. FIG. 6 illustrates a transverse cross section of the catheter 10 shown in FIG. 5 taken along lines 6—6. The tubular open-walled element 12 may be self-expanding, where it assumes the unexpanded diameter configuration in response to the radially compressive force that is applied when the tubular open-walled element 12 is within the lumen 20 of the outer tubular member 16, and assumes the expanded diameter configuration when the tubular open-walled element 12 extends distally of the distal end of the outer tubular member 16 so that the radially compressive force is removed. To expand a tubular open-walled element 12 that is not self-expanding, a radially expansive force, as is produced by inflation of a balloon (not shown) disposed within the tubular open-walled element lumen, would be applied.

In FIG. 1, the occluding member 13 located on the cannula member 18 is shown within the lumen of the outer tubular member, and in FIG. 5 it is shown extended beyond the distal end of the outer tubular member. As best illustrated in FIGS. 1 and 5, when the occluding member 13 extends distally of the distal end of the outer tubular member, the occluding member reversibly occludes the patient's body lumen. In the embodiments illustrated, the occluding member comprises a reversibly expandable protruding collar. However, other suitable occluders exist, including but not limited to, inflatable members, occluding coils, and flexible collapsible membranes. The protruding collar may be concave or convex relative to the distal end of the cannula member, and the flow can be stopped in either direction according to the orientation given the protruding collar. In another embodiment, illustrated in FIG. 12 the occluding member 13 is secured to the tubular open-walled element 12, so that securing the cannula in the patient's body lumen and occlusion of the body lumen are accomplished in one step. In this embodiment, the occluding member 13 cannot be displaced relative to the secured site in the body lumen. Thus, expansion of the tubular open-walled element 12 also causes the occluding member 13 to occlude the patient's body lumen, and retraction of the tubular open-walled element 12 collapses the occluding member 13. In the embodiment illustrated in FIG. 12, the occluding member 13 comprises a flexible collapsible membrane.

In another embodiment of the invention the occluding member 13 is omitted, so that the catheter 10 comprises a shaft 11 comprising outer 16 and inner 17 tubular members, and a cannula member 18, with an expandable tubular open-walled element 12 on the inner tubular member 17.

Figure 7:
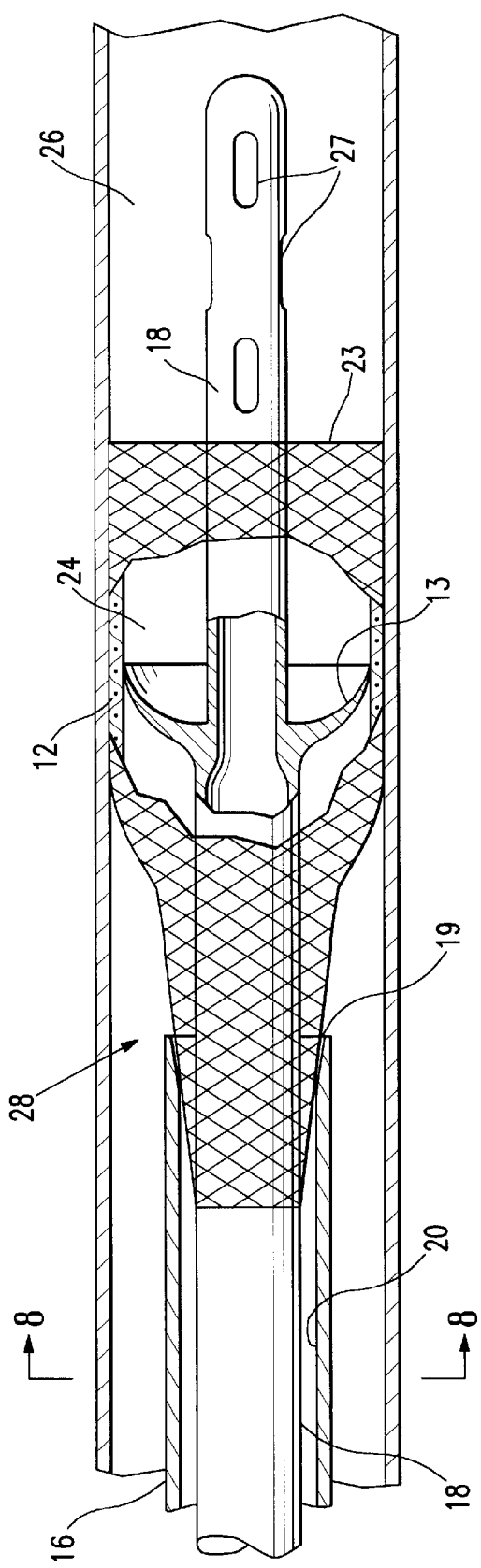
FIG. 7 is an elevational view partially in section of an intraluminal catheter which embodies features of the invention.
Figure 8:
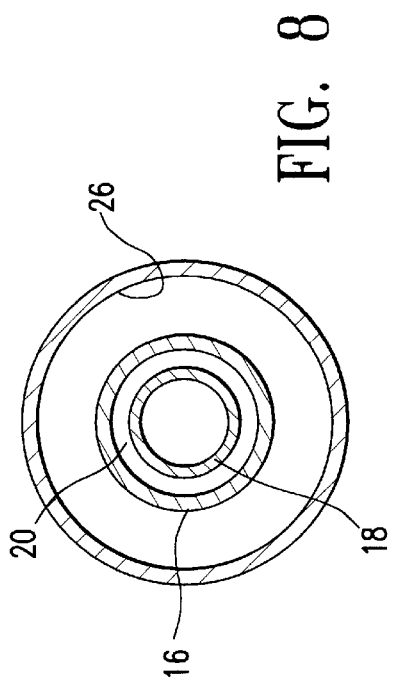
FIG. 8 is a transverse cross-sectional view of the catheter shown in FIG. 7 taken along lines 8–8.

FIG. 7 illustrates another embodiment of the invention, similar to the embodiment illustrated in FIG. 1 except that the inner tubular member is omitted. The catheter 28 comprises an elongated outer tubular member 16 and a cannula member 18 slidably disposed therein. The tubular open-walled element 12 and occluding member 13 are secured to a distal section of the cannula member 18, and are therefore not longitudinally displaceable relative to one another. FIG. 8 illustrates a transverse cross section of the catheter shown in FIG. 7 taken along lines 8—8.

The length of the intraluminal catheter 10/28 for aortic use may be about 20 cm to about 130 cm, and is typically about 40 cm. The inner tubular member 17 and cannula member 18 are sufficiently long to extend out the proximal and distal ends of the outer tubular member. The outer tubular member 16 has an outer diameter (OD) of about 4.0 mm to about 15 mm, and an inner diameter (ID) of about 3.5 mm to about 14 mm. The length of the outer tubular member is about 16 cm to about 125 cm. The inner tubular member 17 has an OD of about 3.5 mm to about 14 mm, and an ID of about 3.30 mm to about 13.4 mm. The length of the inner tubular member 17, including the open-walled element 12 is about 15 cm to about 124 cm. The cannula member 18 has an OD of about 3.3 mm to about 13.4 mm, and an ID of about 3 mm to about 13 mm. The length of the cannula member is about 16 cm to about 135 cm. However, the dimensions of the intraluminal catheter 10/28 will differ depending on the application, as for example, in intraarterial use where the tubular members would have an OD of about 0.5 mm to about 7 mm, and an ID of about 0.3 mm to about 6 mm. The occluding member 13 may be about 7 cm to about 20 cm from the distal extremity of the cannula member 18, typically about 15 cm for the embodiment illustrated in FIG. 1.

The outer tubular member 16, inner tubular member 17, and cannula member 18 may be releasably secured together, so that the members can be longitudinally displaced relative to one another to properly position the tubular open-walled element, occluding member, and cannula member, and then secured together so that the expanded open-walled element is not limited to releasably securing the member on which it is located. Such members may be secured together by a variety of suitable means, including but not limited to clips, outer sheaths, clamps, expandable washers, and the like, on the proximal end of the catheter.

Figure 13:
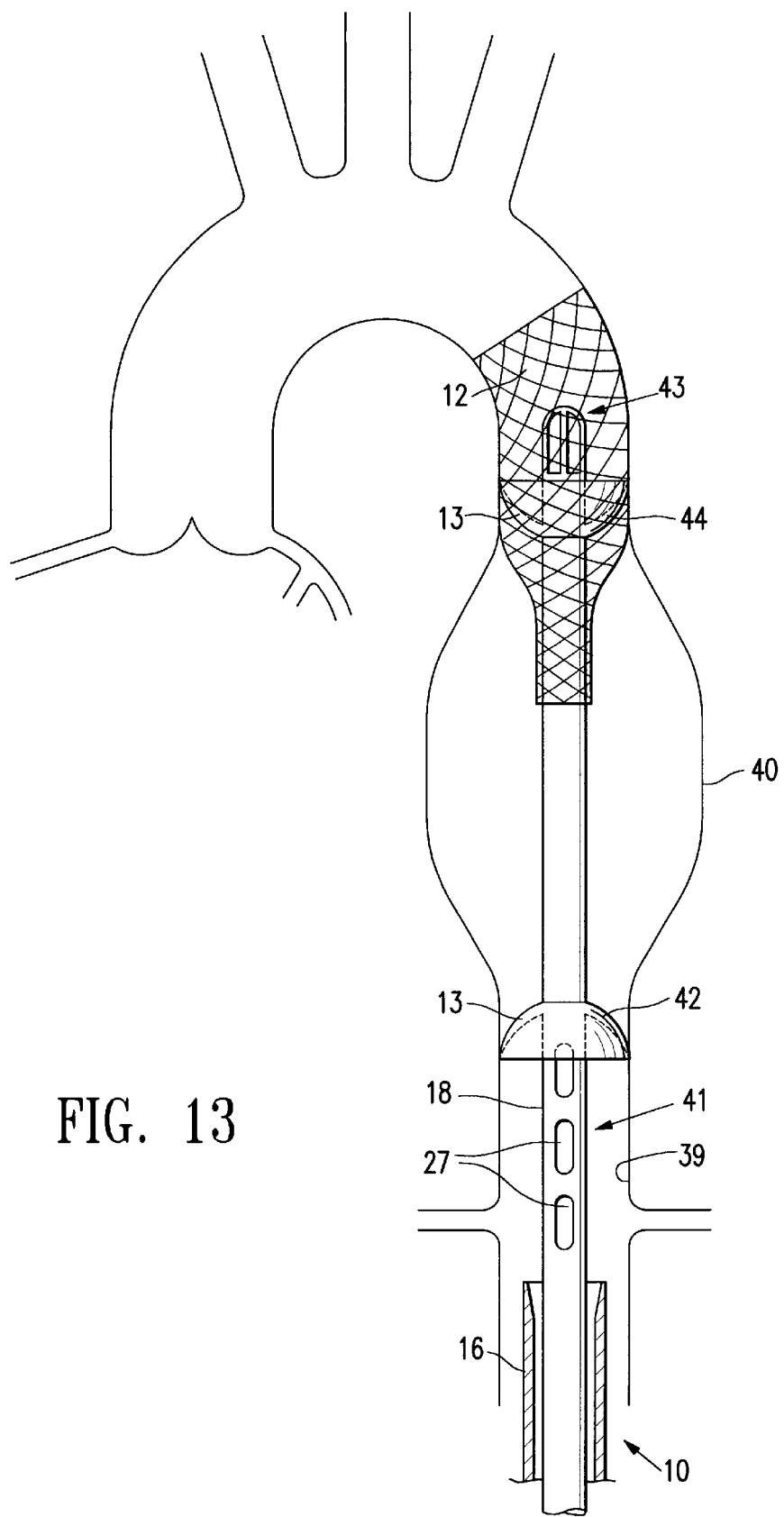
FIG. 13 illustrates an intraluminal catheter which embodies features of the invention disposed within the descending aorta percutaneously.

The cannula member 18 is used for delivering or removing fluids from the body lumen and is provided with at least one perfusion port 27 in fluid communication with the cannula lumen 24. In the embodiments illustrated in FIGS. 1–7, perfusion ports 27 are located on the distal end of the cannula member 17. FIG. 13 illustrates another embodiment, having distal perfusion ports 43 on the distal end of the cannula member 17, and proximal perfusion ports 41 at a location spaced proximally to the distal perfusion ports 43. The perfusion ports may be located proximally or distally to the occluding member 13.

Another aspect of the invention involves a method of performing a medical procedure using the intraluminal catheter 10 of the invention, the method comprising positioning the catheter into a desired location within a patient's body lumen, expanding at least a portion of the open-walled element, wherein the expanded portion of the open-walled element contacts a wall of the lumen at a secured site thereby applying a radially expanding securing force at the secured site sufficient to secure the catheter in the lumen; and performing a medical procedure. Fluid, such as cardioplegic solution, can be delivered from the cannula member to the patient's body lumen.

As described above, the open-walled element 12 is expanded when the member to which it is secured is extended beyond the distal end of the outer tubular member 16 or inner tubular member 17. With a self-expanding tubular open-walled element 12, the step of expanding at least a portion of the open-walled element includes the step of longitudinally separating the inner and outer tubular members so that at least a distal portion of the open-walled element extends distally of the distal end of the outer tubular member. Where the tubular open-walled element 12 is on the cannula member 18, the outer tubular member 16 and cannula member 18 are longitudinally separated to extend the open-walled element distally of the distal end of the outer tubular member 16 of the shaft 11. With a tubular open-walled element 12 that is not self-expanding, the step of expanding at least a portion of the open-walled element includes the step of applying a radially expanding force on the open-walled element so that the open-walled element expands radially. To release the catheter from within the body lumen, the tubular open-walled element 12 is retracted into the outer tubular member lumen or the inner tubular member lumen, depending on whether the open-walled element 12 is on the inner tubular member 17 or the cannula member 18, respectively.

Figure 9:
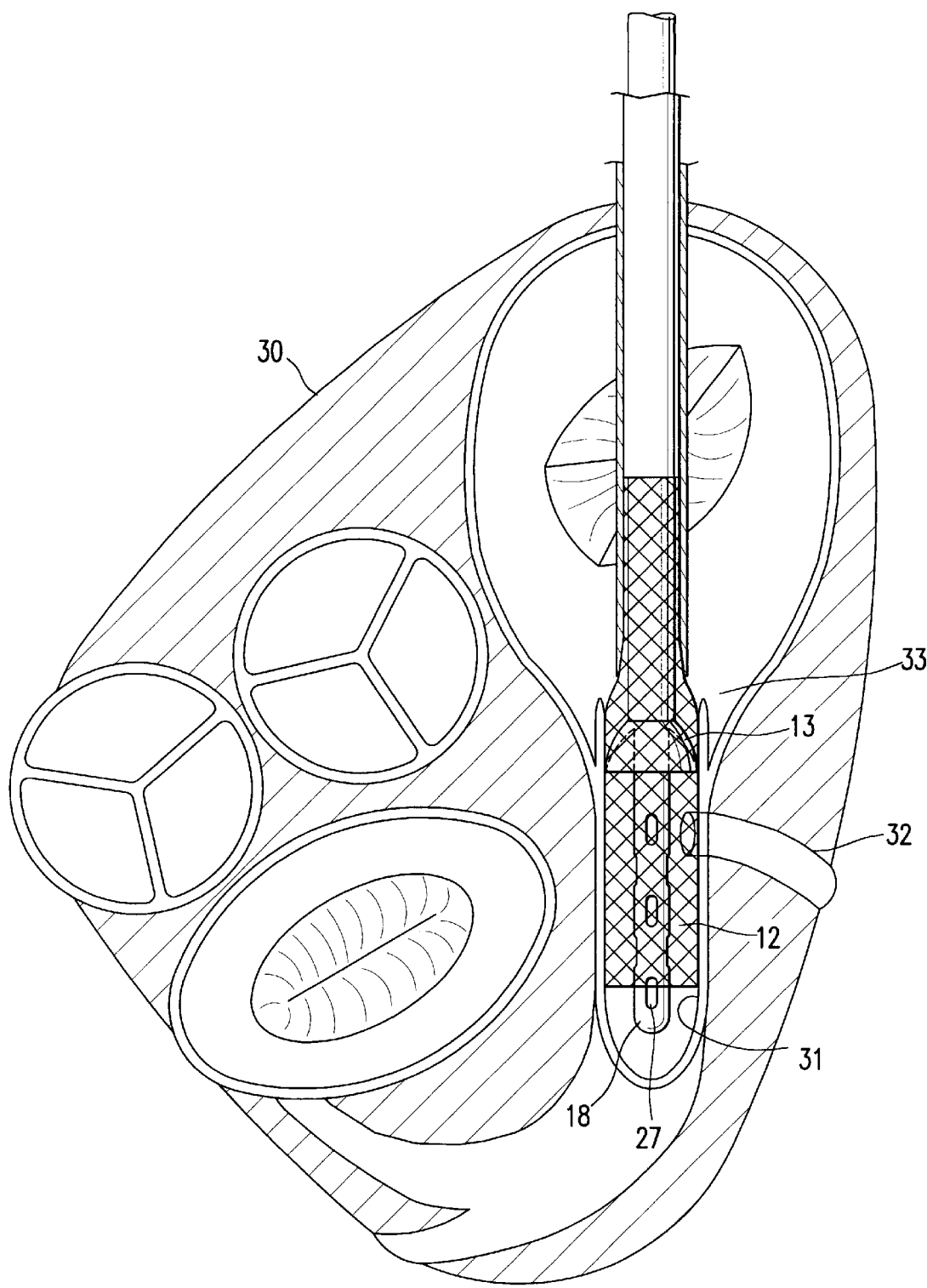
FIG. 9 illustrates an intraluminal catheter which embodies features of the invention disposed in part within a coronary sinus, for retroperfusion of the heart.

In one example, illustrated in FIG. 9, the procedure is retroperfusion of the, heart 30, and the lumen is a coronary sinus 31. The method comprises positioning at least a distal portion of the open-walled element inside the coronary sinus before being expanded, so that the expanded open-walled element applies the radially expanding securing force at an intersection of the coronary sinus 31 and a middle cardiac vein 32 without occluding fluid flow into or out of the middle cardiac vein. The occluding member is positioned inside the coronary sinus to occlude the coronary sinus. The cannula member 18 may be longitudinally displaced relative to the expanded tubular open-walled element to position the perfusion ports 27 and occluding member 13 at the desired location. The cardioplegia solution can then be delivered out the cannula perfusion ports 27 for full retroperfusion of the heart 30. A distal pressure port (not shown) can be provided to measure the pressure in the sinus. The cannula member 18 can be positioned by direct insertion into the right atrium 33, using palpation or a Doppler probe inside the cannula, to direct the cannula and locate the flow from the venous sinus. Surgical insertion is generally accomplished by the use a malleable stylet. Alternatively, the cannula member 18 can be inserted percutaneously over a guidewire. The guidewire is slidably received in a guidewire lumen which extends to a port in the distal end of the cannula. Fluoroscopy can be used to direct the cannula.

Figure 10:
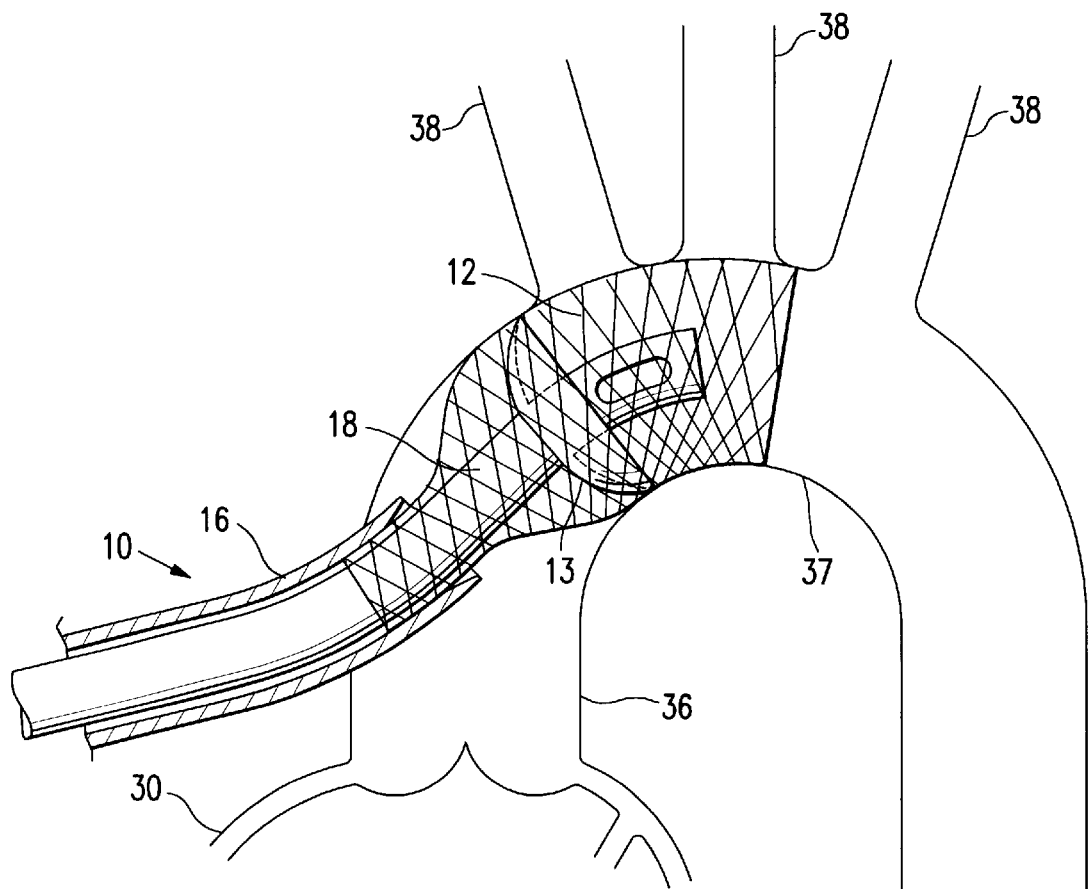
FIG. 10 illustrates an intraluminal catheter which embodies features of the invention disposed in the ascending aorta, by dissection of the ascending aorta.
Figure 11:
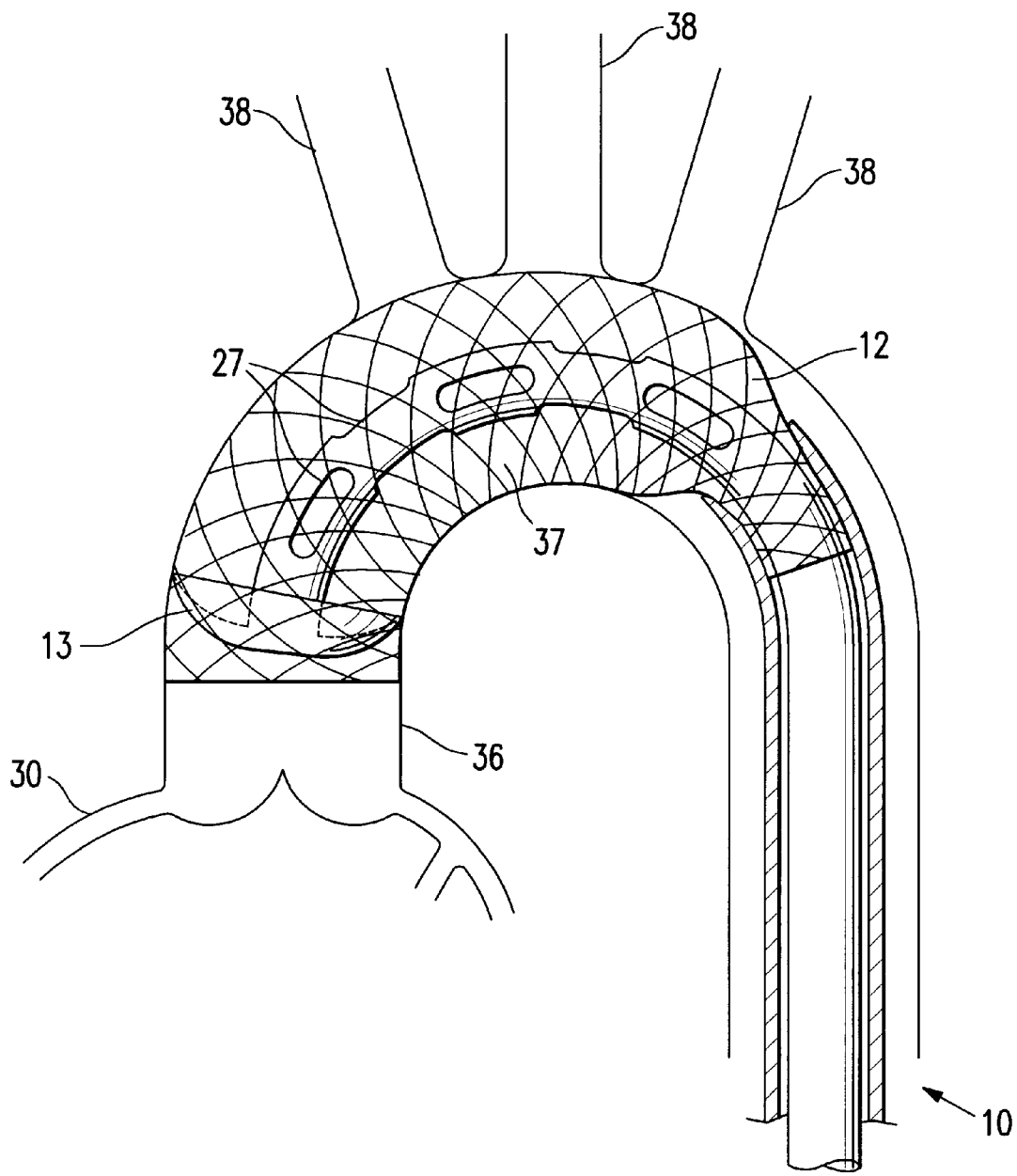
FIG. 11 illustrates an intraluminal catheter which embodies features of the invention disposed within the ascending aorta, by percutaneous introduction of the catheter.
Figure 12:
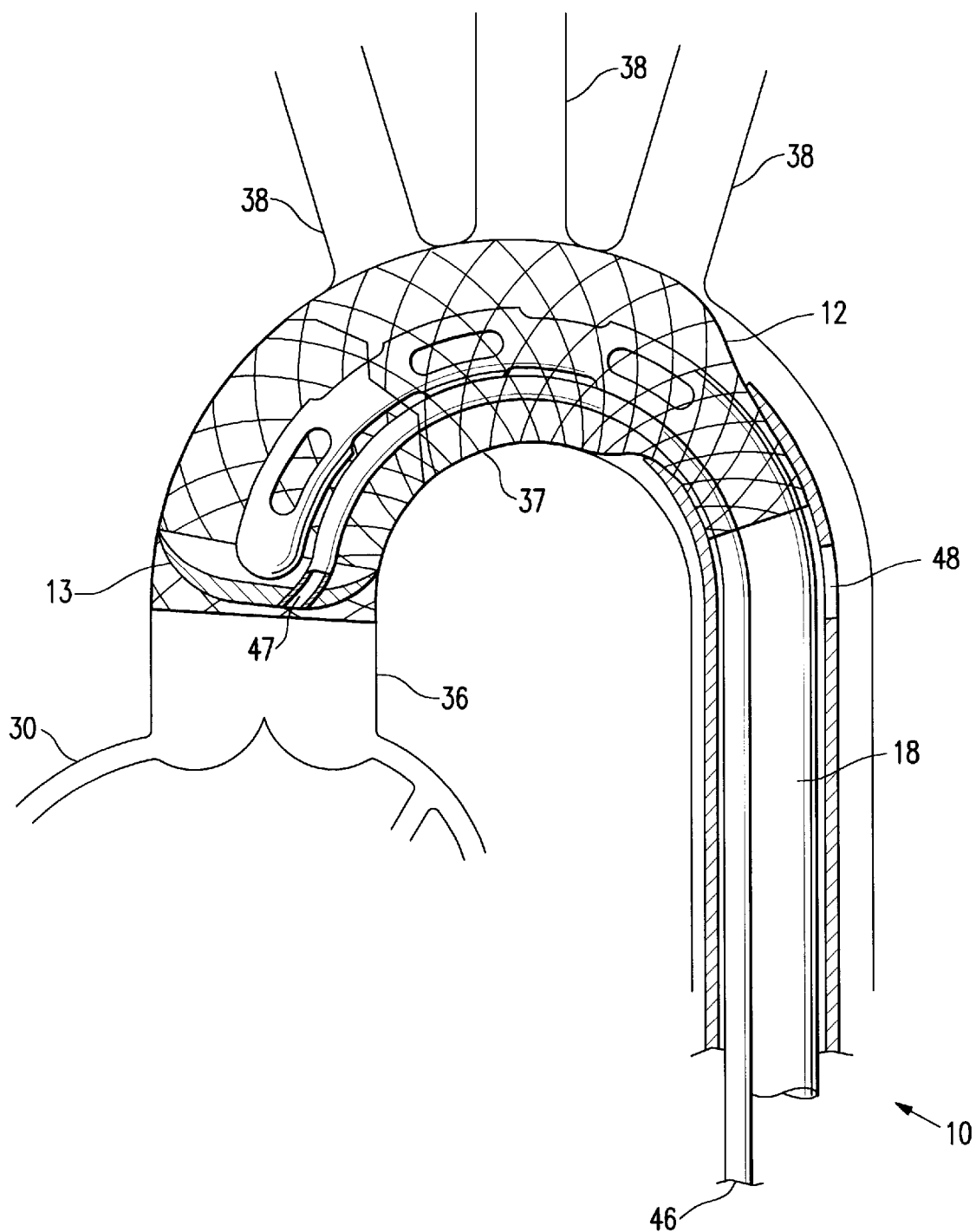
FIG. 12 illustrates an intraluminal catheter which embodies features of the invention disposed within the ascending aorta, by percutaneous introduction of the catheter.

In another example, illustrated in FIGS. 10–12, the procedure is perfusion of the ascending aorta 36. The method comprises introducing the catheter 10 in the aorta, and positioning the distal portion of the open-walled element 12 in the aortic arch 37 at the supra aortic branches 38 before expanding the open-walled element 12. The open-walled element 12 is expanded to secure the catheter 10 within the aorta, so that the expanded open-walled element 12 does not occlude fluid flow into or out of the supra aortic branches 38. FIG. 10 illustrates a catheter 10 introduced by dissection of the ascending aorta 36, and FIG. 11 illustrates a catheter 10 introduced percutaneously into the ascending aorta 36. Because the occluding member 13 is positioned upstream to the supra aortic branches 38 to thereby prevent back flow into the heart, the perfusion ports 27 on the cannula member 18 are located distally to the occluding member 13 when the catheter 10 is introduced by dissection to deliver the solution to the supra aortic branches 38. The perfusion ports 27 are located proximally to the occluding member 13 when the catheter 10 is introduced percutaneously.

In the aortic cannula illustrated in FIGS. 11 and 12, the outer tubular member 16 distal end may be provided with side ports 48, to allow flow across the perfusion ports 27 when the cannula member 18, the occluding member 13, and open-walled element 12 are fully disposed in the outer tubular member 16 lumen. In another embodiment of the invention, the aortic cannula illustrated in FIGS. 10, 11, 12 is provided with an anterograde solution infusion lumen 46 and port 47 (FIG. 12) for anterograde cardioplegic injection in the aortic root, and for venting the left ventricle and aortic root area after the surgery is concluded. To restart the heart after surgery, the occluder is withdrawn while maintaining perfusion. This is achieved by positioning the outer tubular member of the shaft over the occluding member and/or the tubular open-walled member. In the embodiments illustrated in FIGS. 11 and 12, perfusion is maintained via the side port 48 in the outer tubular member, which allows flow from the cannula ports 27 to the patient's body lumen despite the outer tubular member 16 being fully disposed distally over the cannula ports 27. The anterograde port 47 would be located proximally of the occluding member 13 on the aortic cannula illustrated in FIG. 10, and distally of the occluding member 13 in the percutaneous aortic cannula illustrated in FIG. 11.

In another example, illustrated in FIG. 13, the procedure is the treatment of aneurysms in a segment of the aorta requiring positioning of a shunt that bypasses the segment to be treated 40. The catheter is introduced into the descending aorta 39 and a pair of occluding members 13 on the cannula member 18 are positioned on either end of the segment to be treated 40. The tubular open-walled element 12 is expanded within the descending aorta 39 by longitudinally retracting the outer tubular member 16 over the cannula member 18, to secure the cannula member 18 within the descending aorta 39. The cannula member 18 has plurality of perfusion ports 27, one group 41 located proximally to the proximal occluding member 42 and a second group 43 located distally to the distal occluding member 44. The cannula member 18 can be introduced proximal or distal to the segment to be treated 40. Occlusion of the segment 40 allows for its shunting and decompressing before the segment 40 is exposed.

While use of the catheter of the invention has been discussed in terms of vascular procedures, nonvascular applications exist, including but not limited to, prolonged endotracheal intubation which avoids the risk of tracheal necrosis induced by long term balloon compression of the tracheal wall, and tracheoesophageal fistula isolation. While the invention has been described herein in terms of certain preferred embodiments, modifications and improvements may be made to the invention without departing from the scope thereof.

What is claimed is:
1. An intraluminal perfusion catheter, comprising:
a) an elongated shaft having a lumen;
b) an elongated cannula member slidably disposed within the lumen of the shaft;
c) a radially expandable tubular, open-walled, anchoring element which has a proximal end secured to either the cannula member or the elongated shaft, a distal open unsecured end and which is configured to contact a wall defining at least in part a body lumen in an expanded condition and to thereby releasably secure at least part of the catheter the body lumen; and
d) a radially expandable occluding collar secured to the cannula for occluding the body lumen.

2. The intraluminal catheter of claim 1 wherein the collar is on an outer surface of the cannula.

3. An intraluminal perfusion catheter, comprising:
a) an elongated shaft having a lumen;
b) an elongated cannula member slidably disposed within the lumen of the shaft;
c) a radially expandable tubular open-walled anchoring element which has a proximal end secured to the cannula member or the elongated shaft, a distal open unsecured end and which is configured to contact a wall defining at least in part a body lumen in an expanded condition and to thereby releasably secure at least part of the catheter to the body lumen; and
d) a radially expandable occluding collar longitudinally displaceable within the lumen of the shaft, extendable from the shaft lumen to an extended position for occluding the body lumen.

4. The catheter of claim 3 wherein the cannula includes a proximal end, a distal end a port at the distal end which is distal to the occluding collar and an infusion lumen extending within the cannula to and in fluid communication with the port at the distal end.

5. The catheter of claim 3 wherein the occluding collar is secured to the cannula member.

* * * * *

UNITED STATES PATENT AND TRADEMARK OFFICE
CERTIFICATE OF CORRECTION

PATENT NO. : 6,709,415 B2
DATED : March 23, 2004
INVENTOR(S) : Jose Antonio Navia and Jorge Luis Jordana It is certified that error appears in the above-identified patent and that said Letters Patent is hereby corrected as shown below:

<u>Title page,</u>
Item [73], please delete "[73] Assignee: BioSud, S.A., Buenos, Aires (AR)".

Signed and Sealed this

Sixth Day of July, 2004

JON W. DUDAS
*Acting Director of the United States Patent and Trademark Office*